United States Patent [19]
Hijikata et al.

[11] Patent Number: 4,727,033
[45] Date of Patent: Feb. 23, 1988

[54] ANALYZING APPARATUS AND METHOD FOR IMMUNOLOGICAL AGGLUTINATION REACTIONS

[75] Inventors: Kazuo Hijikata; Hajime Sakuma, both of Hachioji; Yutaka Kato, Tama; Hidehiko Yamamoto, Hachioji, all of Japan

[73] Assignee: Olympus Optical Co., Ltd., Tokyo, Japan

[21] Appl. No.: 752,009

[22] Filed: Jul. 5, 1985

Related U.S. Application Data

[63] Continuation of Ser. No. 449,750, Dec. 14, 1982, abandoned.

[30] Foreign Application Priority Data

Dec. 17, 1981 [JP] Japan ................... 56-204190

[51] Int. Cl.4 .................................. G01N 33/86
[52] U.S. Cl. ......................... 436/69; 356/39; 422/65; 422/73
[58] Field of Search ............... 141/67, 105, 163, 178, 141/130, 171, 237, 239, 270, 279; 73/864.11; 356/39, 244, 246; 422/63–67, 73, 100; 436/66, 69, 43, 48

[56] References Cited

U.S. PATENT DOCUMENTS

| 3,489,525 | 1/1970 | Natelson | 422/64 |
| 3,544,272 | 12/1970 | Vaills | 422/65 |
| 3,578,412 | 5/1971 | Martin | 422/65 |
| 3,607,094 | 9/1971 | Beer | 141/105 X |
| 3,617,222 | 11/1971 | Matte . | |
| 3,708,264 | 1/1973 | Jottier . | |
| 3,843,323 | 10/1974 | Quame | 436/48 X |
| 3,883,308 | 5/1975 | Matte | 436/45 X |
| 3,897,216 | 7/1975 | Jones | 422/65 X |
| 3,985,507 | 10/1976 | Litz et al. | 422/65 |
| 4,154,795 | 5/1979 | Thorne . | |
| 4,170,625 | 10/1979 | Welch | 422/64 |
| 4,291,986 | 9/1981 | Satou et al. | 422/67 X |
| 4,319,882 | 3/1982 | Sharma . | |
| 4,411,295 | 10/1983 | Nutter | 141/237 X |

FOREIGN PATENT DOCUMENTS

| 2627237 | 12/1977 | Fed. Rep. of Germany | 422/65 |
| 55-71951 | 5/1980 | Japan . | |
| 55-146044 | 11/1980 | Japan | 422/73 |
| 56-2560 | 1/1981 | Japan | 422/73 |
| 56-96246 | 8/1981 | Japan | 436/43 |

Primary Examiner—Barry S. Richman
Assistant Examiner—Michael S. Gzybowski
Attorney, Agent, or Firm—Parkhurst & Oliff

[57] ABSTRACT

An apparatus for analyzing blood samples by detecting particle agglutination patterns formed on inclined bottom surfaces of reaction vessels formed in a microplate includes a diluted sample preparing section for delivering given amounts of blood cells and serum contained in a sample tube into diluting vessels mounted on a sample plate secured on a rotating endless belt and for discharging predetermined amount of a diluent into the diluting vessels to form diluted blood cell and serum samples, a diluted sample delivering section for delivering given amounts of the diluted blood cell and serum samples contained in the diluting vessels into an array of reaction vessels of the microplate in a selective manner according to test-items to be analyzed and a reagent delivering section for discharging given reagents into the reaction vessels. The microplate having the diluted blood cell and serum samples delivered therein is fed in a substantially stationary manner along a reaction line arranged in a vertical plane and in this reaction line the particle patterns formed on the reaction vessel bottoms are photoelectrically detected.

19 Claims, 14 Drawing Figures

FIG_4
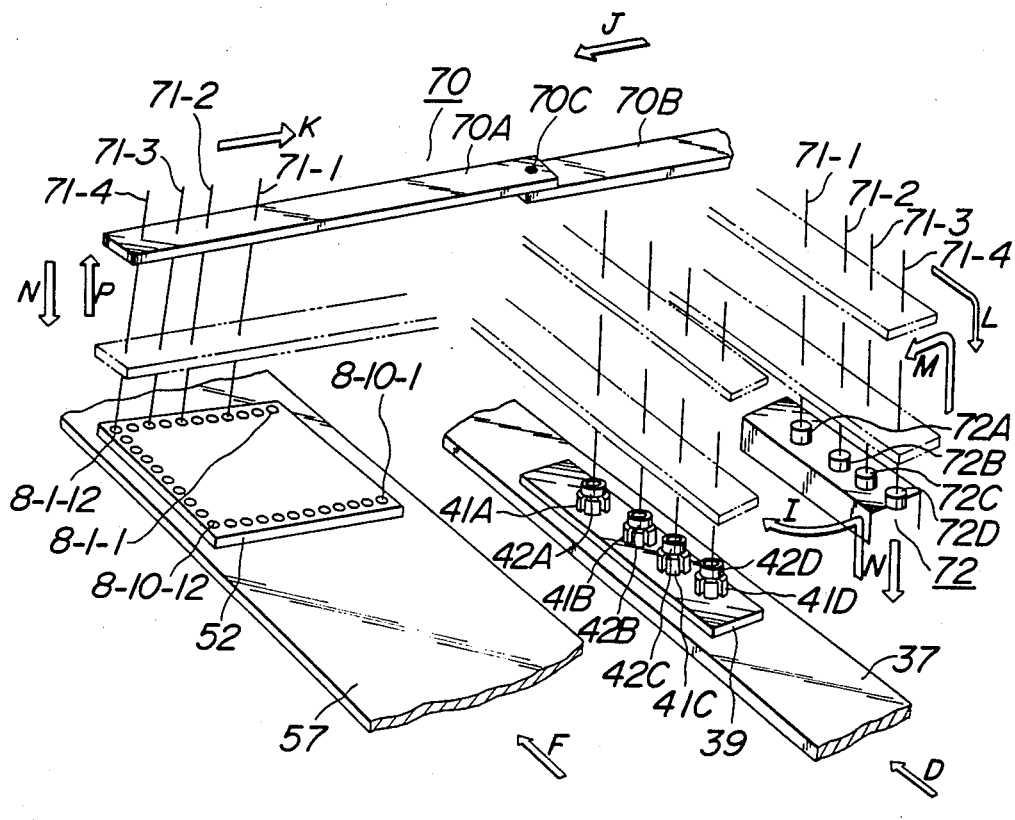
FIG_5
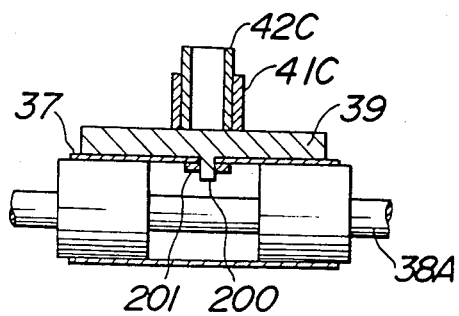

FIG_11A
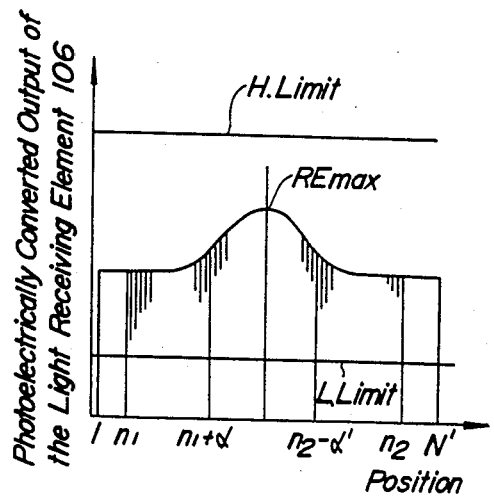
FIG_11B
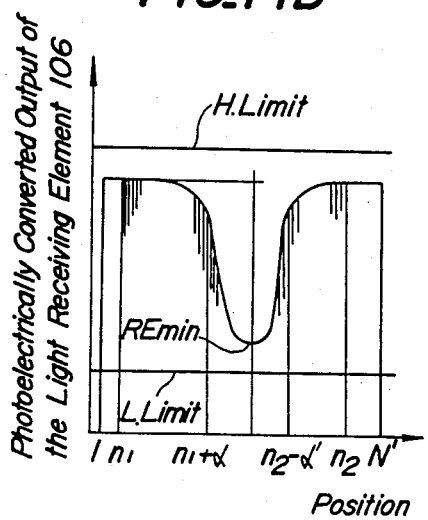

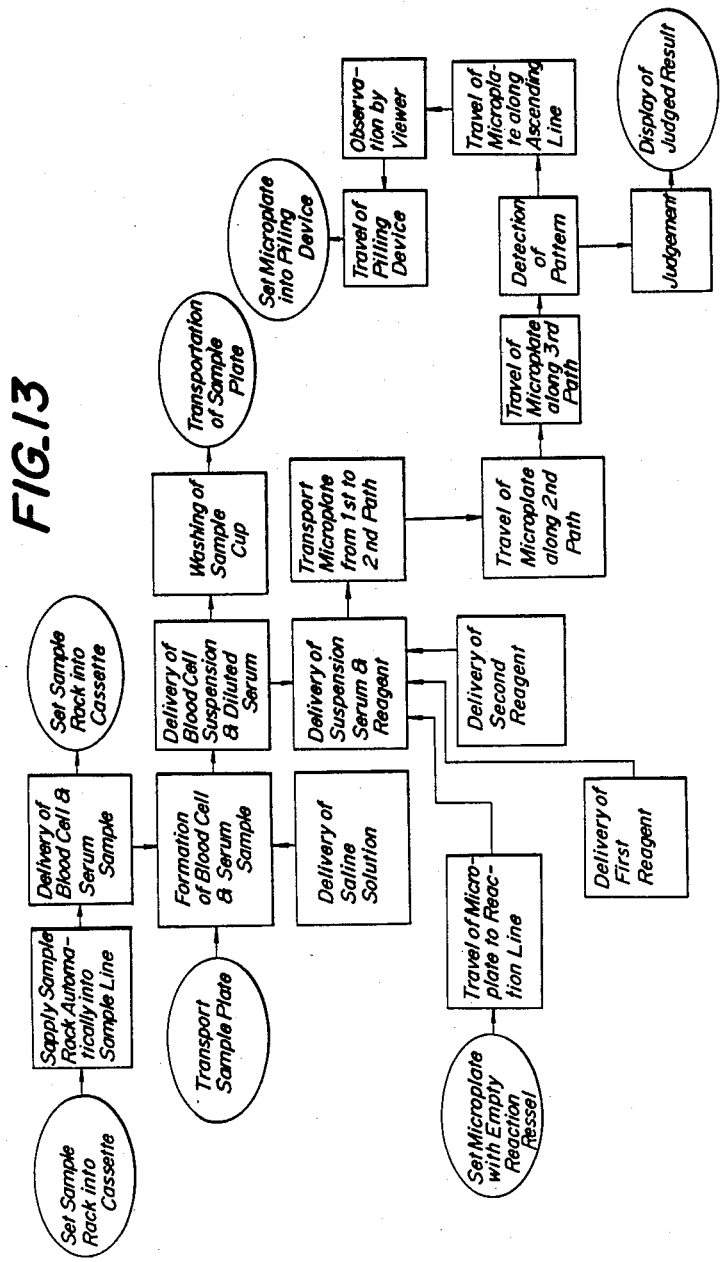

ANALYZING APPARATUS AND METHOD FOR IMMUNOLOGICAL AGGLUTINATION REACTIONS

This is a continuation of application Ser. No. 449,750 filed Dec. 14, 1982, now abandoned.

BACKGROUND OF THE INVENTION

This invention relates to an agglutination analyzing apparatus for analyzing agglutination patterns produced in response to an immunological agglutination reaction, and more particularly to an apparatus for identifying various kinds of blood types with the aid of agglutination patterns of blood corpuscles or for detecting various kinds of antibodies and various antigens in sample solutions (like viruses, proteins or the like) with the aid of agglutination patterns of not only blood corpuscles but also of particles of materials such as latex, carbon or the like.

In known analyzing apparatuses due to the agglutination reaction, reaction vessels and analyzing steps are different for respective components to be analyzed. For instance, in a known manual method for judging the blood type of ABO system, use was made of test tubes as the reaction vessels. In this method a sample blood is first contrifuged to separate red blood cells and serum from each other, and then a given amount of blood cells is mixed with a diluent to form a blood cell suspension of 2 to 5%. Then, a given amount of the blood cell suspension is delivered into a test tube into which anti-A-serum or anti-B-serum is also distributed. After the blood cells have been centrifuged, the test tube is shaken and it is confirmed with the naked eye whether or not agglutination is formed. In this case, the sample blood which produces agglutination together with A-type antibody, but does not produce agglutination together with B-type antibody is identified as A-type, the sample blood which produces agglutination exclusively with B-type antibody is judged to be B-type, the sample blood which forms agglutination with both A-type and B-type antibodies is determined to be AB-type, and sample blood which does not produce agglutination with either A-type and B-type antibodies is judged as O-type.

In order to detect and measure HBs antigen, a method has been proposed which makes use of a plastic plate, called a microplate, provided with a number of wells, i.e. reaction vessels each having a conical base surface. This conventional method makes use of a microplate having 10×12 wells, for example, and detects and prescribes the HBs antigen by the following procedure.

(1) Buffer solution specially prescribed for R-PHA method is introduced into each well of the microplate one drop (0.025 ml) at a time.

(2) A test serum (0.025 ml) is added to the first well of a row. By using a diluter, the doubling dilution is performed along the row up to the last (tenth) well.

(3) One drop of R-PHA buffer (0.025 ml) is added to a first row and one drop of R-PHA inhibition solution is added to a second row.

(4) After the mixtures thus treated have been sufficiently agitated by a micromixer for 10 seconds, incurvation is effected for one hour at 37° C.

(5) A drop of R-PHA cells of 1% suspension (0.025 ml) is added to each well.

(6) The mixtures are agitated by the micromixer for ten seconds to suspend the R-PHA cells uniformly.

(7) After the mixtures thus treated have been made stationary at room temperature for one hour, agglutination patterns are detected.

In the T-PHA system for syphilis, different diluents of a sample serum are formed in the microplate and a reagent prepared by bonding syphilis viruses with red blood cells of sheep is added to the serum diluents. After natural segmentation, it is confirmed with the naked eye whether or not agglutination is formed.

As described above, in the analyzing methods due to immunological agglutination reaction different kinds of reaction vessels are used depending upon the test items and further successive steps are also different for respective items.

There has also been known a microtiter method in which use is made of the microplate as the reaction vessels and steps are partially automated. In this method, delivery of samples and reagents and detection of agglutination are carried out automatically, but other steps are effected manually. This is due to the fact that in the case of using the microplate, mechanism and operations are liable to be complicated and thus, it is extremely difficult to effect all the steps automatically. Further, the microtiter method has several disadvantages. Since the sample serum is delivered quantitatively with the aid of capillary phenomenon, it is necessary to first deliver diluent into each well in the microplate and then a tip of dilutor onto which a sample has been applied is immersed into the diluent to mix the serum and diluent. Such a step is very complicated as compared with normal delivery steps in the analyzing apparatuses and thus could be controlled only by means of complicated mechanisms. Further, the delivery amount is made always constant, because the capillary action is utilized and thus, the delivery amount could not be adjusted at will. Further, the mixed solution is applied to the dilutor and the sample is partially wasted. This becomes a serious drawback in a multi-item analyzer.

Moreover, if the delivery of the blood cell sample is effected before the serum sample delivery, an indefinite amount of the blood cell sample might be removed from the well. Therefore, in the microtiter system, the diluent delivery, serum delivery and blood cell delivery have to be performed in this order and thus, the mechanical arrangement or design might be restricted. Further, in the microtiter method, since use is made of the blood cell suspension of about 1%, the operation is liable to be very complicated as compared with the test tube method described above.

In a conventional method of identifying blood types, for example, which has heretofore been proposed, use was made of a winecup-shaped reaction vessel into which was quantitatively introduced a sample solution, i.e. 2 to 5% of test blood corpuscles suspended in saline solution, and a specified antiserum, i.e. anti-A- or anti-B-serum. Then, the mixture was held stationary for reaction between blood corpuscles and antiserum. Subsequently, it was centrifuged to sediment blood corpuscles. Then, the reaction vessel was rapidly wobbled such that the sedimented blood corpuscles were forcedly separated one from the other and then relatively slowly wobbled so as to collect the clumped compositions in the center portion of the base surface of the vessel and form settling patterns, thereby photometrically detecting these patterns.

Such conventional blood type identifying method in which sedimentation is effected and then the reaction vessel is rapidly wobbled so as to separate the sedimented blood corpuscles from the base surface of the vessel can only be applied to the analysis of regular ABO blood type, which shows strong agglutination, but could not be applied to many other immunological agglutination reactions which show weak agglutination, for example, a method of determining Rh blood subtype or detecting various kinds of incomplete antibodies. That is, if the agglutination reaction is weak, the blood corpuscles or the like which have been clumped together become separated one from other when the reaction wheel is wobbled, and as a result, the particles are not collected in the center portion of the reaction vessel.

Further, in this known method, in order to effect the accurate judgement of the blood type, it is necessary to prepare a substantial amount of the sample blood cells and thus, required amounts of standard antiserums are increased accordingly. Nowadays, a very large number of test items are to be effected for respective patients and thus, required amounts of the sample blood for respective items must be decreased as small as possible.

The applicant has proposed in a Japanese Patent Application Laid-open Publication No. 146,044/80 a blood type judging method in which not only blood types due to natural antibodies showing strong agglutination, but also blood types due to incomplete antibodies having weak agglutination can be judged very precisely, while necessary amounts of the blood samples can be minimized. In this method, use is made of reaction vessels having conical bottom surfaces and blood cells in blood samples to be analyzed are delivered into the reaction vessels together with standard antiserum reagents. After sufficiently mixing the samples and reagents, the mixtures are kept stationary for a relatively short time such as thirty minutes and then agglutination patterns formed on the bottom surfaces of reaction vessels are detected to identify the blood type. In this method, when the sample blood cells react with the antiserum, blood cells settling down on the inclined bottom surface of reaction vessel are combined with each other and are deposited uniformly on the bottom just like as snow. When the blood cells do not react with the antiserum, the settling cells are not agglutinated and roll down along the inclined bottom surface and are collected at the lowest bottom center. Therefore, by photoelectrically detecting the patterns formed by blood cells settled on the bottom surface, it is possible to identify the blood type. According to this method, since the reaction vessels are kept stationary during the reaction and detection steps, various kinds of antibodies and antigens such as HBs antigen and syphilis antibody can be effectively detected.

However, the known analyzer for effecting the above method has still several drawbacks in that the analyzer becomes large in size and that the treating ability is low, because only a small number of samples can be set in the analyzer at one time.

SUMMARY OF THE INVENTION

The present invention has for its object to provide an analyzing apparatus for an immunological agglutination reaction which can effect an immunological analysis in a precise and efficient manner.

It is another object of the invention to provide an analyzing apparatus which can selectively identify various types of substances such as red blood cell type, white blood cell type, blood disc type and lymphocyte type and further can selectively direct various kinds of antigens, antibodies, viruses and specific proteins.

It is still another object of the invention to provide an analyzing apparatus which can be made simple in construction and small in size.

According to the invention, an apparatus for analyzing blood samples due to immunological agglutination reaction comprises:

means for carrying a plurality of sample tubes which accommodate blood samples to be analyzed therein at a sample delivery position in turn, each sample tube including blood cells and serum separated from each other;

means for carrying a plurality of diluting vessels through said sample delivery position, a diluted sample delivery position and a washing position;

means for forming at least one diluted blood cell sample and at least one diluted serum sample by delivering the blood cells and serum contained in a sample tube situating at the sample delivery position into at least two diluting vessels situating at the sample delivery position together with a diluent;

a reactive line including a plurality of reaction line passages extended in the horizontal and vertical directions in the same vertical plane;

means for feeding microplates having a number of reaction vessels successively from input side of the reaction line;

means for delivering given amounts of the diluted blood cell and serum samples contained in the diluting vessels situating at the diluted sample delivery position into a plurality of reaction vessels of the microplate supplied on the reaction line;

means for delivering given amounts of the reagents into the reaction vessels according to the analysis-item to be tested;

means for transporting microplates having blood samples and reagents delivered in the reaction vessels along the reaction line in a substantially stationary manner;

means for photoelectrically detecting agglutination patterns formed on the inclined bottom surfaces of the reaction vessels at a measuring position on the reaction line due to antigen and antibody reaction of the blood cell and serum samples and the reagent;

means for receiving the detection signal to effect an analysis due to the existence and non-existence of the agglutination patterns;

means for discharging the microplates from an exit of the reaction line after the agglutination patterns of all the reaction vessels in the microplate have been detected; and means for washing the diluting vessels at the washing position to prepare for a next blood sample diluting operation.

BRIEF DESCRIPTION OF THE DRAWINGS

FIG. 4 is a perspective view for explaining a sample delivering mechanism according to the invention;

FIG. 5 is a cross sectional view showing one embodiment of a connecting mechanism between an endless belt and a sample plate;

FIGS. 11A and 11B are schematic views respectively depicting an output pattern of a light receiving device shown in FIG. 10;

FIG. 13 is a flow chart depicting successive procedures of the analyzing apparatus shown in FIG. 2.

DESCRIPTION OF THE PREFERRED EMBODIMENTS

In this invention, a microplate including a plurality of reaction vessels is moved with respect to a sample delivering means, a reagent delivering means and a photometering means and is traveled in a substantially stationary manner along a reaction line in horizontal and vertical directions, the reaction line having a plurality of reaction line paths arranged in a vertical plane. After a predetermined time period from sample and reagent deliveries, an agglutination pattern generated on a bottom surface of the reaction vessel which is traveled in a stationary state is detected by the photometering means. In the conventional microtitor method, it is necessary to sediment particles in a reaction vessel under a complete stationary condition after the sample and reagent deliveries are effected. Therefore, in order to automate the operations mentioned above it is necessary to transfer the reagent and sample delivering means and agglutination detection means with respect to the stationary reaction vessel, and thus the apparatus becomes large and complicated. According to the applicant's experiments, if the microplate is transferred at the same speed as that of the conventional biochemical analyzer, a formation of the particle agglutination pattern due to a natural sedimentation is not affected by a vibration or a movement of the microplate, and thus it is possible to form an accurate agglutination pattern on the bottom surface of the microplate. Therefore, the vessel traveling for use in the conventional biochemical analyzer may be assumed to be substantially stationary in the immunological agglutination reaction. Further, since a plurality of reaction vessels are arranged on one microplate, the traveling mechanism becomes extremely simple and also a processing efficiency becomes high. Especially, since the microplate is traveled along the reaction line including a plurality of reaction line paths arranged in a vertical plane, it is possible to make the analyzing apparatus small in size.

Moreover, since respective samples are delivered into a plurality of reaction vessels to form a plurality of agglutination patterns and are judged synthetically, it is possible to perform an extremely accurate analysis. The apparatus according to the invention is used, for example, in the blood testing center, and if an erroneous judgement is occurred n the blood analysis a great accident is occurred immediately. Therefore, it is very important to make an analysis accuracy high.

Hereinafter, the present invention will be explained in detail with reference to the drawings.

Figure 1:
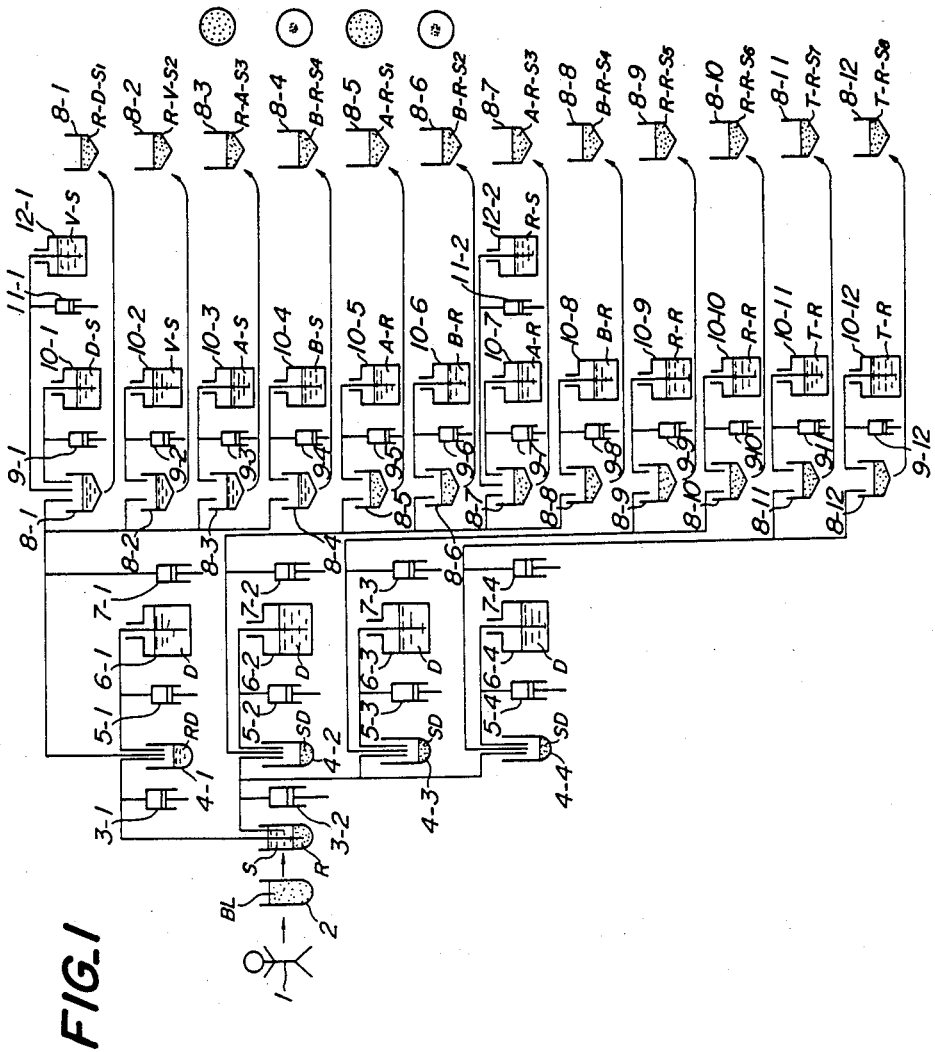
FIG. 1 is a schematic diagram for explaining successive steps of an analyzing method for use in an analyzing apparatus due to an immunological agglutinating reaction according to the invention.

FIG. 1 is a schematic diagram for explaining successive steps of an analyzing method for use in the analyzing apparatus due to an immunological agglutinating reaction according to the invention. A whole blood BL extracted from a patient 1 is contained in a test tube 2. The tube 2 is set in a known centrifuge with an anticoagulant such as sodium citrate and the whole blood BL is separated into a serum S and blood cells (red blood cells) R. Then, blood cells R are aspirated by a delivering device 3-1 constituted by a micro-syringe and is delivered into a sample cup 4-1 into which a diluent D such as saline solution contained in a vessel 6-1 is also delivered by means of a delivering device 5-1. In this manner, in the cup 4-1, there is contained a blood cell suspension RD. By means of a delivering device 3-2, the serum S in the tube 2 is delivered into samples cups 4-2, 4-3 and 4-4 into which are also delivered by delivering devices 5-2, 5-3 and 5-4 the diluent D so as to form a diluted serum SD.

Next, the blood cell suspensions RD and SD contained in the sample cups 4-1 to 4-4 are quantitatively delivered into reaction vessels 8-1 to 8-12 (No. 1 channel to No. 12 channel) each having a conical bottom surface by means of delivering devices 7-1 to 7-4. In addition, predetermined reagents corresponding to the test-items contained in first reagent vessels 10-1 to 10-12 are quantitatively delivered into the reaction vessels 8-1 to 8-12 by means of other delivering devices 9-1 to 9-12. Further, predetermined reagents contained in second reagent vessels 12-1 and 12-2 are quantitatively delivered into the reaction vessels 8-1 and 8-7 by other delivering devices 11-1 and 11-2, respectively, so that required sample solutions are formed in the reaction vessels 8-1 to 8-12.

In this manner, in the reaction vessel 8-1, the blood cell suspension RD in the sample cup 4-1 is delivered by the delivering device 7-1, and also anti-D-serum (diluted with phosphoric buffer) D-S in the first reagent vessel 10-1 is delivered by the delivering device 9-1 and a bromelin (diluted with phosphoric buffer) V-S in the second reagent vessel 12-1 is delivered by the delivering device 11-1, so that sample solution R-D-S$_1$ is obtained. In the reaction vessel 8-2, the blood cell suspension RD in the sample cup 4-1 is delivered by the delivering device 7-1 and also the bromelin (diluted with phosphoric buffer) V-S in the first reagent vessel 10-2 is delivered by the delivering device 9-2, so that sample solution R-V-S$_2$ is obtained. In the reaction vessel 8-3, the blood cell suspension RD in the sample cup 4-1 is delivered by the delivering device 7-1 and also anti-A-serum (diluted with saline solution) A-S in the first reagent vessel 10-3 is delivered by the delivering device 9-3, so that sample solution R-A-S$_3$ is obtained. In the reaction vessel 8-4, the blood cell suspension RD in the sample cup 4-1 is delivered by the delivering device 7-1 and anti-B-serum (diluted with saline solution) B-S in the first reagent vessel 10-4 is delivered by the delivering device 9-4, so that sample solution R-B-S$_4$ is obtained. In the reaction vessel 9-5, the diluted serum SD in the sample cup 4-2 is delivered by the delivering device 7-2 and A-type blood cell reagent (diluted with saline solution) A-R in the first reagent vessel 10-5 is delivered by the delivering device 9-5, so that sample solution A-R-S$_1$ is obtained. In the reaction vessel 8-6, the diluted serum SD in the sample cup 4-2 is delivered by the delivering device 7-2 and B-type blood cell reagent (diluted with saline solution) B-R in the first reagent vessel 10-6 is delivered by the delivering device 9-6, so that sample solution B-R-S$_2$ is obtained. In the reaction vessel 8-7, the diluted serum SD in the sample cup 4-2 is delivered by the delivering device 7-2, and also A-type blood cell reagent (diluted with saline solution) A-R in the first reagent vessel 10-7 and blood cell reagent R-S in the second reagent vessel 12-2 are delivered by the delivering devices 9-7 and 11-2, respectively, so that sample solution A-R-S$_3$ is obtained. In the reaction vessel 8-8, the diluted serum SD in the sample cup 4-2 is delivered by the delivering device 7-2 and B-type blood cell reagent (diluted with saline solution) B-R in the first reagent vessel 10-8 is delivered by the delivering device 9-8, so that sample solution B-R-S$_4$ is obtained. In the reaction vessel 8-9, the diluted serum SD in the sample cup 4-3 is delivered by the delivering device 7-3 and blood cell sensitized with R-PHA buffer R-R in the first reagent vessel 10-9 is delivered by the delivering device 9-9, so that sample solution R-R-S$_5$ is obtained. In the reaction vessel 8-10, the diluted serum SD in the sample cup 4-3 is delivered by the delivering device 7-3 and blood cells sensitized with R-PHA buffer R-R in the first reagent vessel 10-10 is delivered by the delivering device 9-10, so that sample solution R-R-S$_6$ is obtained. In the reaction vessel 8-11, the diluted serum SD in the sample cup 4-4 is delivered by the delivering device 7-4 and blood cells sensitized with T-PHA buffer T-R in the first reagent vessel 10-11 is delivered by the delivering device 9-11, so that sample solution T-R-S$_7$ is obtained. In the reaction vessel 8-12, the diluted serum SD in the sample cup 4-4 is delivered by the delivering device 7-4 and blood cells sensitized with T-PHA buffer T-R is delivered by the delivering device 9-12, so that sample solution T-R-S$_8$ is obtained.

As mentioned above, sample solutions in the respective reaction vessels 8-1 to 8-12 and test-items based on the agglutination patterns of these sample solutions are as follows.

| Test-item | Reaction vessel (channel No.) | | First reagent | Sample | Second reagent | Sample solution |
|---|---|---|---|---|---|---|
| RH-type blood | 8-1 | 1 | Anti-D-serum (diluted with phosphoric buffer) D-S | Blood suspension (diluted with saline solution) | Bromelin (diluted with phosphoric buffer) | R-D-S$_1$ |
|  | 8-2 | 2 | Bromelin (diluted with phosphoric buffer) V-S | Blood suspension (diluted with saline solution) |  | R-V-S$_2$ |
| ABO-type blood | 8-3 | 3 | A-type blood cell reagent (diluted with saline solution) A-S | Blood suspension (diluted with saline solution) |  | R-A-S$_3$ |
|  | 8-4 | 4 | B-type blood cell reagent (diluted with saline solution) B-S | Blood suspension (diluted with saline solution) |  | R-B-S$_4$ |
|  | 8-5 | 5 | Anti-A-serum (diluted with saline solution) A-R | Diluted serum (diluted with saline solution) |  | A-R-S$_1$ |
|  | 8-6 | 6 | Anti-B-serum (diluted with saline solution) B-R | Diluted serum (diluted with saline solution) |  | B-R-S$_2$ |
| Antibody screening | 8-7 | 7 | A-type blood cell reagent (diluted with saline solution) A-R | Diluted serum (diluted with saline solution) | Blood cell reagent | A-R-S$_3$ |
|  | 8-8 | 8 | B-type blood cell reagent (diluted with saline solution) B-R | Diluted serum (diluted with saline solution) |  | B-R-S$_4$ |
| HBs antigen | 8-9 | 9 | Blood cells sensitized with R-PHA R-R | Diluted serum (R-PHA buffer) |  | R-R-S$_5$ |
|  | 8-10 | 10 | Blood cells sensitized with R-PHA R-R | Diluted serum (R-PHA buffer) |  | R-R-S$_6$ |
| Syphilis antibody | 8-11 | 11 | Blood cells sensitized with T-PHA T-R | Diluted serum (T-PHA buffer) |  | T-R-S$_7$ |
|  | 8-12 | 12 | Blood cells sensitized with T-PHA T-R | Diluted serum (T-PHA buffer) |  | T-R-S$_8$ |

In this embodiment mentioned above, the reaction vessel is wobbled when the diluted serum or the blood suspension and the reagent are delivered into the reaction vessels 8-1 to 8-12. However, when both solutions to be delivered are sufficiently mixed with each other in case that the diluted serum or the blood suspension and the reagent are delivered, it is not necessary to wobble the reaction vessel any more. After such wobbling for agitation (including the vibration of the reaction vessel, between solutions, etc.), the microplate having a plurality of reaction vessels must be traveled along the reaction line stationarily, so that the test liquids are not subjected to hard shock so as to allow the reaction to proceed stably. During the reaction, the blood cell particles are sedimented naturally. This reaction time period is determined by taking into account of diluted rates, diluted amount of blood cells or serum and reagent amount and further reaction between them, and is, for example, about 10 to 60 minutes.

If it is assumed that the sample blood is of A-type, the blood cells are agglutinated each other for the sample solution $R-A-S_3$ to which the anti-A-serum A-S is supplied, and are sedimented on the inclined bottom surface of the reaction vessel 8-3 uniformly. Contrary to this, the blood cells are not agglutinated in the sample solution $R-B-S_4$ including the anti-B-serum B-S, and are rolled down along the inclined bottom surface of the reaction vessel 8-4 to be collected at the lowest center of the bottom surface. In this manner, as shown in FIG. 1, in case of agglutination, the blood cells settling on the inclined bottom surface of the vessel form a uniformly deposited pattern and in case of non-agglutination, the settling blood cells do not remain on the inclined surface, but are collected at the bottom center so as to form an integrated pattern. These patterns can be detected photoelectrically so as to judge the blood type.

In the reaction vessel 8-6, there is no agglutination and the integrated pattern is formed at the bottom center of vessel, while in the reaction vessel 8-5 the agglutination occurs so that the uniformly deposited pattern is formed on the bottom surface. By photoelectrically detecting these patterns it is also possible to judge the blood type. The judgement just explained above is generally referred to as indirect judgement. By effecting both the direct and indirect judgements, the type of the sample blood can be judged very accurately. In case of using the microplate having formed therein a number of reaction vessels in a matrix form, the microplate is removed from the reaction line after the patterns formed on the bottoms of the whole reaction vessels have been detected.

In the above embodiment shown in FIG. 1, the reagents A-S, B-S, A-R and B-R are delivered into the reaction vessels after the blood cell and serum samples have been delivered. It should be noted that the order of delivery of these reagents and samples may be reversed or the reagents and samples may be delivered simultaneously.

In the blood type judging method explained above, since the reaction vessels are placed quietly and the agglutination patterns, i.e. the uniformly deposited pattern and the integrated pattern are formed by natural sedimentation of blood cells, the blood type having weak agglutination force due to incomplete antibodies can be identified very accurately. Contrary to this, in the known method, the blood cells once agglutinated might be separated from each other by vibrating the reaction vessel. Further in the above method, the blood cell suspension is sufficient to have a very small concentration such as 0.5 to 2% and an amount of suspension is enought to be small as 5 to 30 $\mu$. Therefore, an amount of the sample blood can be very small. Contrary to this, in the known method, a great amount of blood cell suspension of 2 to 5% is required. It should be noted that the above method is not limited to determining the blood type of A, B, O-system, but may be equally applied to judge other blood types and to various immunological analyses.

Figure 2:
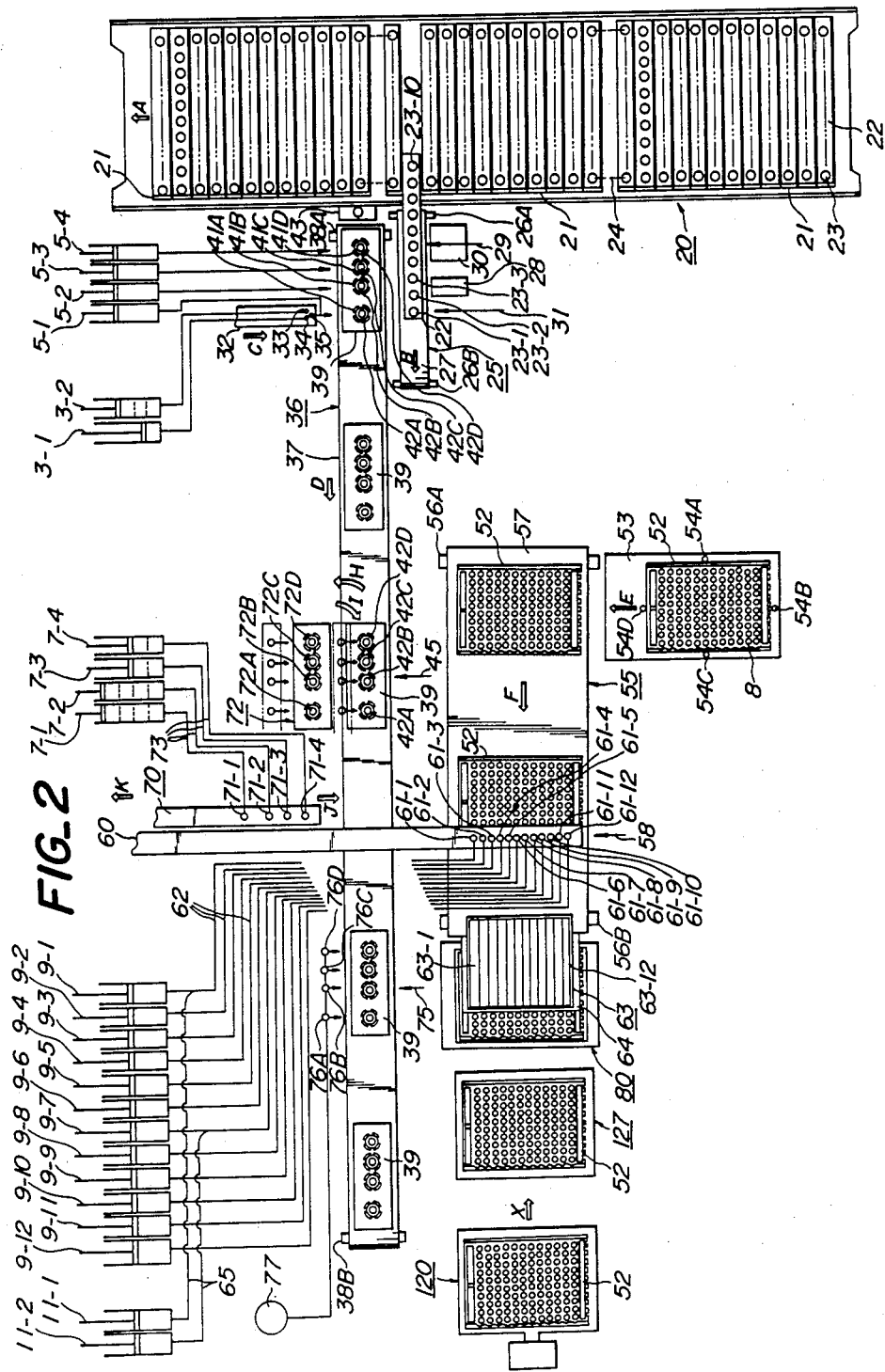
FIG. 2 is a schematic plan view illustrating an embodiment of the analyzing apparatus according to the invention.

FIG. 2 is a schematic plan view showing an embodiment of the analyzing apparatus according to the invention. A reference numeral 20 generally denotes a sampler comprising three rack cassettes 21 in each of which twelve sample racks 22 are set. Each rack includes ten sample vessels or tubes 23. Therefore, one sample rack cassette contains 120 sample tubes 23. A centrifuged sample blood is supplied into each sample tube 23, and to a side wall thereof is adhered a bar code which indicates sample information such as patient number, test-items, blood-type, etc.

The rack cassette 21 is fed in a direction shown by an arrow A at a given pitch along a sample guide line 24 arranged in the sampler 20. When the rack 22 in the rack cassette 21 reaches a sample suppling line 25, the rack 22 is moved in a direction shown by an arrow B by means of a feed claw mechanism (not shown) in the sampler 20 and is mounted on an endless belt 27 which is moved at a given speed by driving shafts 26A, 26B. The rack 22 on the endless belt 27 is traveled to a sample detecting position 29 comprising a sample detecting device 30 by a rack positioning device 28. At first, the bar code of the first sample tube 23-1 is read out, and then the rack 22 is traveled intermittently to the position where next sample tube 23-2 is located on the sample detecting position 29 by means of the rack positioning device 28. After that, the bar code of the sample tube 23-2 is read out by the sample detecting device 30. As for the rack positioning device 28, it is possible to arrange claws connected to a solenoid which function to stop the movement of the rack 22 against a moving force in the arrow B direction or to stop it in synchronism with the endless belt 27. In this manner, sample information is read out successively from the bar codes adhered to respective sample tubes 23-1 to 23-10 in the rack 22.

After detecting the sample information, the reaction tube is further traveled to a sample delivering position 31 successively, and at this sample delivering position 31, for example, the blood cell particles and the serum in the sample tube 23-1 are quantitatively sucked into the delivering devices 3-1 and 3-2 via a blood cell nozzle 33 and a serum nozzle 34 arranged in a tip portion of a sample arm 32. The sucking operation mentioned above is performed in such a manner that the sample arm 32 is moved in a direction shown by an arrow C so as to position the nozzles 33, 34 above the sample tube 23-1 at the delivering position 31 and then is moved downward so as to immerse the tip portions of the nozzles 33 and 34 into the blood cell particles and the serum, respectively. In this embodiment, an electrode 35 is arranged in the tip portion of the sample arm 32 to be immersed into the sample tube 23-1 together with the nozzles 33, 34, and the nozzles 33, 34 are made of conductive material. Therefore, a liquid surface or a boundary surface between the serum and blood cells is detected due to a variation of impedance between these electrodes, and thus it is possible to control the downward operation of the sample arm 32 and to detect whether the test liquid is contained in the sample tube or not.

In this embodiment, a distance between the sample detecting position 29 and the sample delivering position 31 is determined as that from the reaction tube 23-1 to the tube 23-5, but it is a matter of course that the distance is not limited to the embodiment mentioned above.

After sucking the serum and the blood cells quantitatively, the sample arm 32 is moved upward and then moved in an opposite direction with respect to that shown by the arrow C to position the blood cell nozzle 33 and the serum nozzle 34 above a sample guide line 36. In the sample guide line 36, an endless belt 37 made of stainless steel is moved intermittently in a direction shown by an arrow D by means of suitable driving shafts 38A and 38B. To the endless belt 37 are secured a plurality of sample plates 39, and in each sample plate 39 are arranged first holder 41A, second holder 41B positiond at a little apart from the holder 41A, third holder 41C and fourth holder 41D which are located with a constant distance in a direction shown by the arrow D. Moreover, diluting sample cups 42A, 42B, 42C, 42D are detachably inserted into respective holders. The sample cup 42A is arranged for the blood cell particles, and into the sample cup 42A the blood cell particles are discharged by the delivering device 3-1 and at the same time the saline solution contained in a vessel (not shown) is discharged by the delivering device 5-1, so that a predetermined amount of the blood cell suspension (RD) is formed in the sample cup 42A. Next, the sample cup 42B is moved into a position under the sample arm 32 by the endless belt 37, and into the sample cup 42B about one third of the serum sample in the delivering device 3-2 is delivered and at the same time the saline solution in the vessel is discharged by the delivering device 5-2, so that a predetermined amount of the diluted serum (SD) is formed in the diluting sample cup 42B. In the same manner, into the sample cups 42C and 42D the serum sample is delivered via the serum nozzle 34 and a predetermined amount of the saline solution is delivered from the delivering devices 5-3 and 5-4, so that the diluted serum (SD) is formed in the sample cups 42C and 42D.

Then, the sample arm 32 is moved in an opposite direction with respect to that shown by the arrow D so as to be positioned to a washing device 43 arranged near the periphery of the sample guide line 36. The blood cell nozzle 33, the serum nozzle 34 and the electrode 35 are washed at this washing position, and after that the sample arm 32 is returned to the initial position shown in FIG. 2.

The operations mentioned above are performed for all the successive sample tubes at the sample delivering position 31, and thus it is possible to form the blood cell suspension (RD) and the diluted serum (SD) each having a predetermined dilution rate in the sample cups 42A and 42B to 42D arranged successively on the sample plate 39, respectively. In this embodiment, it is assumed that the moving period of the sample rack 22 on the endless belt 27 is 15 seconds. Therefore, during a period of 15+10=150 (seconds) the dilution and delivery operations of the samples are ended with respect to the sample tubes 23-1 to 23-10 arranged in one sample rack 22.

In this embodiment, if the blood cell sample delivery is performed in such a manner that at first the blood cell sample is delivered and then the saline solution is delivered after an elapse of time, the blood cell particles are deposited on the bottom surface of the reaction vessel, and thus it is not possible to perform a good agitation operation. Therefore, it is preferable to finish the delivery of the blood cell sample during a delivering period of the saline solution. Contrary to this, the saline solution delivery for the serum sample can be performed at any position between the serum delivering position and a sample sucking position 45 described hereinafter.

Moreover, in this embodiment, the sample is delivered successively into the sample cups 42A to 42D in synchronism with the movement of the endless belt 37, but in is possible to move the sample arm 32 along the sample guide line 36 so as to position successively the nozzles 33 and 34 above the sample cups 42A to 42D. Moreover, it is possible to deliver the sample by taking into account of the movement of the sample arm 32 and the endless belt 37.

After the sample deliveries for all the sample tubes 23-1 to 23-10 on the sample rack 22, the endless belt 27 is moved in an inverse direction and the sample rack 22 is supplied to the initial position in the sample rack cassette 21. Then, the sample rack cassette 21 is moved by one pitch in the direction shown by the arrow A and the next sample rack is supplied to the sample supplying line 25 and the same operation as mentioned above is performed repeatedly for the next sample tubes.

The sample plate 39 for supporting the sample cups 42A to 42D in which the blood cell suspension (RD) and the diluted serum (SD) are contained is positioned to the sample sucking position 45 by the movement of the endless belt 37.

In the embodiment shown in FIG. 2, a microplate 52 has reaction vessels 8 of 12×10=120 pieces, and positioning notches are formed in one side surface of the microplate along ten reaction vessels arrays. As is explained with reference to FIG. 1, since use is made of twelve reaction vessels (12 channels) for one sample, it is possible to form the sample solutions for ten samples in one piece of the microplate 52. A bottom surface of each reaction vessel 8 has a conical shape and a plurality of steps are formed regularly in a concentric manner to form a stable base layer of the sedimented particles on this inclined bottom surface. Moreover, a cross section of the inclined bottom suface in an inclined direction may be formed as a saw-tooth shape. In this embodiment, it is possible to form a depth of the regular steps uniformly or in successively changing manner along the inclined surface with taking into account of a size of the sedimented particles. Further, the shape of the cross section is not limited to the saw-tooth shape, but it is possible to form the cross section into concave or convex shape. In addition, it is possible to form partly the steps on the inclined bottom surface. Furthermore, the shape of the bottom surface is not limited to the conical shape, but it is possible to form the shape in frusto-conical. In this manner, if the regular steps are formed on the inclined surface, the stable base layer of the sedimented particles is formed on the step portion. Therefore, in case of the agglutination reaction the sedimented particles are deposited uniformly on the base layer, and in case of non-agglutination reaction the sedimented particles are rolled down along the inclined bottom surface and are collected at the lowest bottom center, so that clear agglutination or non-agglutination patterns can be formed on the inclined bottom surface.

A plurality of microplates 52 are piled up on an automatic plate supplying device 53. These plates 52 are positioned by guide members 54A to 54D arranged in the supplying device 53. In FIG. 2, for the sake of simplicity, the lowermost microplate 52 is shown. The microplates 52 piled up on the supplying device 53 are successively traveled in a direction shown by an arrow E at a predetermined timing from the lowermost one, and are mounted on a microplate transferring device 55.

The microplate transferring device 55 comprises an endless belt 57 which is moved in a direction shown by an arrow F by means of driving shafts 56A and 56B in parallel with that of the sample guide line 36. The microplate 52 supplied on the endless belt 57 is moved to a reagent delivering position 58. At the sample and reagent delivering position 58, predetermined reagents are delivered quantitatively into one array of twelve reaction vessels as shown in FIG. 2, and at the same time the blood cell suspension and the diluted serum have been delivered quantitatively from the sample cups 42A to 42D situated at the sample sucking position 45, so that the predetermined sample solutions are obtained.

Further, a reagent arm 60 supports channel nozzles 61-1 to 61-12 corresponding to twelve reaction vessels (twelve channels) situated at the reagent delivering position 58, and these nozzles are connected with the delivering devices 9-1 to 9-12 via respective tubes 62. A reagent vessel 63 has twelve channel vessels 63-1 to 63-12 corresponding to respective channels in which the predetermined first reagents are contained as explained in FIG. 1. Moreover, upper plugs (not shown) are arranged on respective channel vessels 63-1 to 63-12, if necessary, and an agitation device is arranged in respective channels or collectively for preventing a clumping of the reagent and especially the sedimentation of the blood cell reagent. The reagent vessel 63 is provided above the endless belt 57 of the microplate transferring device 55, and further mounted on a reagent plate 64 which is secured to a main body with a space that the microplate 52 can be passed underneath the plate 64. Moreover, 1st channel nozzle 61-1 and 7th channel nozzle 61-7 of the reagent arm 60 are connected with the delivering devices 11-1 and 11-2, respectively, and thus the predetermined second reagents are delivered into the reaction vessels of the microplate 52 corresponding to respective channels as explained in FIG. 1. In FIG. 2, tubes 65 from the delivering devices 11-1 and 11-2 are connected to the tubes 62 corresponding to 1st and 7th channels, respectively, but it is possible to connect these tubes directly to the 1st channel nozzle 61-1 and the 7th channel nozzle 61-7 and also to arrange exclusive second reagent nozzles directly connected to these tubes.

Figure 3:
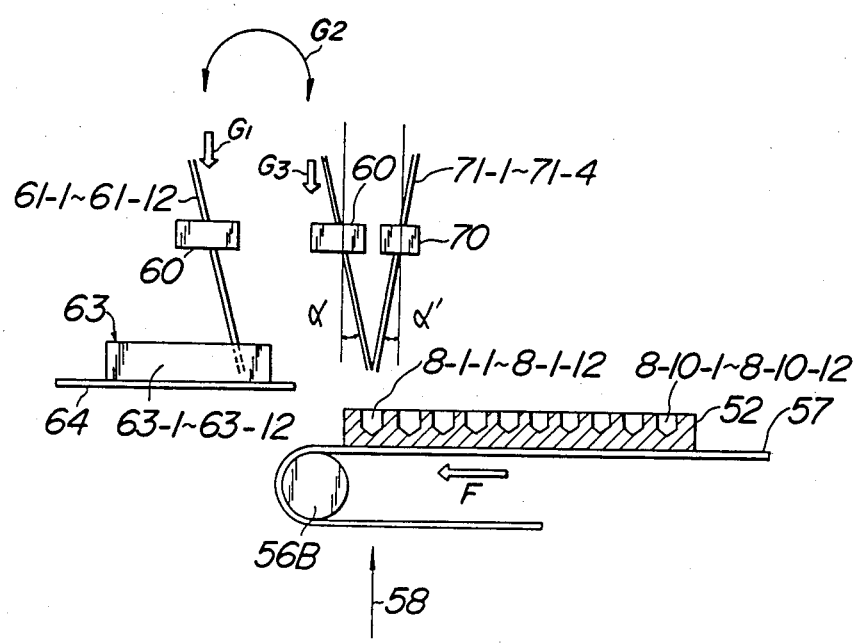
FIG. 3 is a schematic view for explaining a reagent delivering mechanism of the analyzing apparatus shown in FIG. 2.

Hereinafter, an operation of the reagent arm 60 and a relation between the reagent vessel 63 and the microplate 52 will be explained with reference to FIG. 3. The channel nozzles 61-1 to 61-12 are secured to the reagent arm 60 at a little deviation angle $\alpha$ in an anti-clockwise direction with respect to a vertical direction as shown in FIG. 3. Moreover, sample delivering nozzles 71-1 to 71-4 are secured to a sample delivering arm 70 at the sample and reagent delivering position 58 with a deviation angle $\alpha'$. The sample delivering arm will be explained hereinafter. Into reaction vessels 8-1-1 to 8-1-12 on the microplate 52 which are traveled intermittently by the endless belt 57 are delivered at the delivering position 58 the first reagent (and the second reagent), the blood cell suspension and the diluted serum via the channel nozzles 61-1 to 61-12 and the sample delivering nozzles 71-1 to 71-4 to form the sample solutions, and then the agglutination reaction is started. At first, the reagent arm 60 is moved downward in a direction shown by an arrow $G_1$, and the tip portions of the channel nozzles 61-1 to 61-12 are immersed into corresponding reagent vessels 63-1 to 63-12. Under such a condition, the reagents in the reagent vessels 63-1 to 63-12 are sucked by the corresponding channel nozzles 61-1 to 61-12. Then, the reagent arm 60 is moved upward and is traveled along an arc as shown by an arrow $G_2$, and is further moved downward in a direction shown by an arrow $G_3$ to effect a predetermined delivery of the reagent.

Next, the sample delivering arm 70 will be explained. In the embodiment shown in FIG. 2, four sample delivering nozzles 71-1 to 71-4 are arranged on the sample delivering arm 70 at a predetermined interval corresponding to the sample cups 42A to 42D in the sample plate 39 traveled at the sample sucking position 45 by the endless belt 37, and these nozzles are connected with the delivering devices 7-1 to 7-4 via respective tubes 73. When the sample plate 39 reaches the sample sucking position 45, the sample delivering arm 70 is turned by about 90° in the horizontal plane in a direction shown by an arrow H like a two-dotted chain line by means of a universal driving mechanism (not shown) and is moved downward. Then, the sample delivering nozzles 71-1 to 71-4 are immersed into respective sample cups 42A to 42D positioned at the sample sucking position 45. Under such a condition, the blood cell suspension in the sample cup 42A is sucked by the delivering device 7-1 via the nozzle 71-1, and also the diluted serums in the sample cups 42B to 42D are sucked by the delivering devices 7-2 to 7-4 via the nozzles 71-2 to 71-4. The sample delivering arm 70 is then moved upward to the predetermined position to get out the sample nozzles 71-1 to 71-4 from the sample cups 42A to 42D, and is moved in an arrow I direction along an arc as well as in an arrow J direction toward the microplate 52. In this position, at first the diluted serum in the delivering device 7-4 is delivered into the reaction vessel 8-n-12 (n is selected from 1 to 10) on the microplate 52 via the sample delivering nozzle 71-4. Then, in a course of returning the sample delivering arm 70 in an arrow K direction, the diluted serum in the delivering device 7-4 is delivered into the reaction vessel 8-n-11 via the nozzle 71-4, the diluted serum in the delivering device 7-3 is delivered into the reaction vessels 8-n-10 and 8-n-9 via the nozzle 71-3, the diluted serum in the delivering device 7-2 is delivered into the reaction vessels 8-n-8, 8-n-7, 8-n-6 and 8-n-5 via the nozzle 71-2 and the blood cell suspension in the delivering device 7-1 is delivered into the reaction vessels 8-n-4, 8-n-3, 8-n-2 and 8-n-1 via the nozzle 71-1.

It is preferable to perform substantially simultaneously the reagent delivery from the channel nozzles 61-1 to 61-12 in the reagent arm 60 to the reaction vessels 8-n-1 to 8-n-12 and the blood cell suspension and the diluted serum deliveries from the sample delivering nozzles 71-1 to 71-4 in the sample delivering arm 70 to the reaction vessels 8-n-1 to 8-n-12, while a processing efficiency of the analysis, a reaction speed and an agitation efficiency in case of delivering are taken into account of. That is to say, the following delivering process may be conceived, (1) delivering the reagent into the reaction vessels 8-n-1 to 8-n-12 at the same time, and then delivering the samples while the sample delivering arm 70 is moved in the arrow K direction in a swift manner, (2) delivering the reagent into the reaction vessels 8-n-1 to 8-n-12 successively, and delivering the samples successively corresponding to the reagent delivery and (3) delivering the reagents into the reaction vessel groups each consisting of a few vessels successively, and delivering the sample correspondingly.

After effecting the sample delivery, the sample delivering arm 70 is moved in the arrow K direction to a predetermined position and then rotated again in the arrow H direction. The sample delivering arm 70 is further moved to nozzle washing portions 72A to 72D arranged corresponding to the sample delivering nozzles 71-1 to 71-4 so as to wash the respective nozzles therein. The sample delivering arm 70 is moved repeatedly along the locus mentioned above to perform the sample delivery. In this embodiment, the reagent and the sample deliveries for one array of the reaction vessels 8-n-1 to 8-n-12 are performed for 15 seconds. Therefore, the formation of the sample solution for one microplate 52 is effected during a time period of $15 \times 10 = 150$ seconds.

Then, an operation and a positional relation of the sample delivering arm 70, the microplate 52 and the same plate 39 will be explained with reference to FIG. 4. The sample delivering arm 70 comprises a delivering arm portion 70A and a supporting arm portion 70B. The delivering arm portion 70A is rotated about a supporting shaft 70C and these arms 70A, 70B can be moved together in the arrow K direction and also in the arrow J direction. The washing operation of the sample delivering nozzles 71-1 to 71-4 is effected in the nozzle washing portions 72A to 72D of the washing device 72 arranged near the endless belt 37. For instance, after the delivering arm 70 is moved downward in an arrow L direction and the washing of the nozzles 71-1 to 71-4 is effected, the delivering arm 70 is moved upward and then is moved toward the sample line 25 in an arrow M direction to be positioned at a sample sucking position of the sample cups 42A to 42D. At this position, the delivering arm 70 is moved downward in an arrow N direction to perform a predetermined sucking operation, and after that the arm 70 is further moved upward in an arrow I direction and is rotated along an arc into a position aligned with the arrow J direction. After the arm 70 is moved in the direction J, the delivering arm 70 is moved downward in an arrow N direction to effect the sample delivery for the successive reaction vessels from 8-n-12 to 8-n-1 on the microplate 52, and after that the arm 70 is moved upward in an arrow P direction and then returned in an arrow K direction into the initial direction. In this manner, one cycle of delivery operation is ended.

The diluting sample cups 42A to 42D from which the diluted blood cell suspension and the diluted serum are sucked into the sample delivering nozzles 71-1 to 71-4 are then moved to a washing position 75 by the endless belt 37, as shown in FIG. 2. In this washing position 75, washing nozzles 76A to 76D are arranged so as to be immersed in the sample cups 42A to 42D, and the samples remained in the sample cups 42A to 42D are discharged by an operation of a suction pump 77 via these nozzles. After that, a washing liquid is delivered into the sample cups 42A to 42D by a washing liquid supplying means (not shown) via washing nozzles 76A to 76D to wash the sample cups 42A to 42D. The sample cups 42A to 42D after washing are dried during the movement thereof on the endless belt 37, and are further traveled to the sample delivering position 31 again so that the sample cups are used repeatedly. In this embodiment, respective sample plates 39 are secured to the endless belt 37 by means of a stud 200 provided on a bottom of the sample plate 39 and a nut 201 as shown by a cross section in FIG. 5.

The microplate 52 into which are delivered the reagents and the samples is further traveled in the arrow F direction. In this embodiment, since the agglutination reaction is started from the formation of the sample solution, it is assumed hereinafter that the endless belt 57 is called a first reaction line path. As shown in FIG. 2, a microplate descending device 80 is arranged almost beneath the reagent plate 64 on which the reagent vessels 63 are placed. The microplate descending device 80 will be explained with reference to FIGS. 6 and 7.

Figure 6:
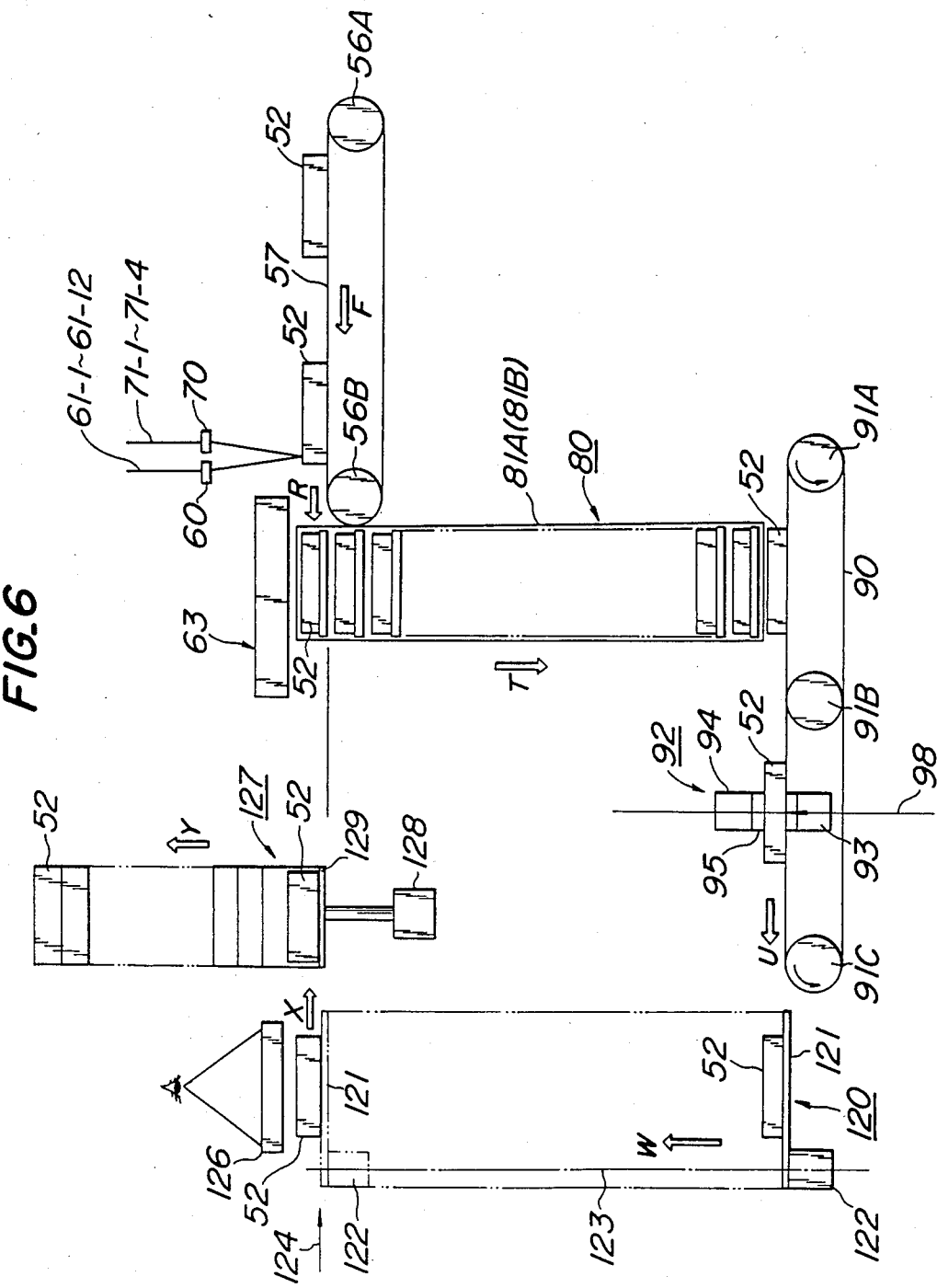
FIG. 6 is a schematic view for explaining a microplate transferring mechanism according to the invention.
Figure 7:
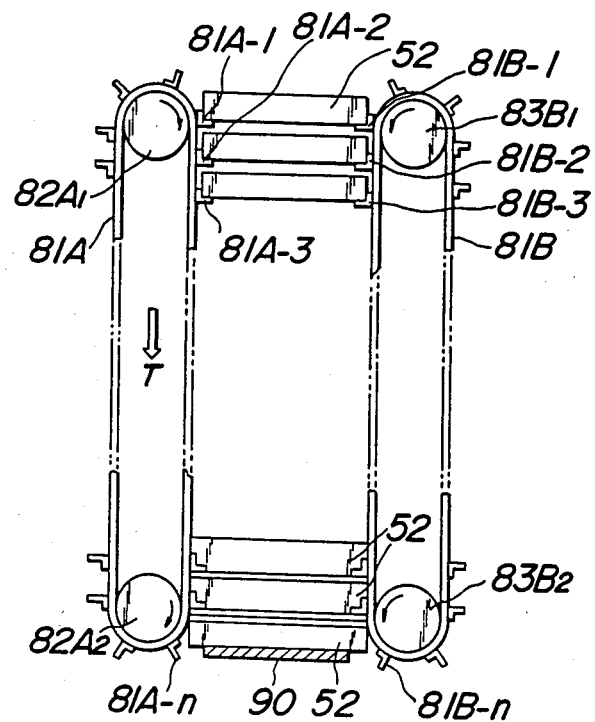
FIG. 7 is a schematic view showing a microplate descending mechanism according to the invention.

In FIGS. 6 and 7, the microplate 52 on the endless belt 57 which is rotated by means of the driving shafts 56A, 56B is traveled in the direction shown by the arrow F. Then, the microplate 52 is supported between a pair of endless supporting belts 81A, 81B of the microplate descending device 80. A plurality of L-shaped plates 81A-n and 81B-n for positioning a number of the microplates therebetween are secured at an equal distance to the supporting belts 81A, 81B. Moreover, these plates have stoppers (not shown) for preventing the microplate 52 from falling down from the plates. The supporting belts 81A and 81B are rotated in opposite directions by means of driving shafts $82A_1$, $82A_2$ and $83B_1$, $83B_2$ which are rotated at a constant speed by a given driving means. Therefore, the miroplates 52 successively supplied from the endless belt 57 are supported between pairs of L-shaped plates, and is traveled successively in an arrow T direction in dependence upon a rotation of the supporting belts 81A and 81B. In this traveling line, the agglutination reaction of the sample solutions contained in the reaction vessels of the microplate is performed. In this embodiment, this vertical traveling line is called second reaction line path. Since the agglutination reaction is effected in the second reaction line path, it is necessary to move the supporting belts 81A, 81B quietly without subjecting the microplates to hard shock. The lowermost microplate 52 fed between the supporting belts 81A and 81B is transported onto an endless belt 90 when the L-shaped plates 81A-n and 81B-n supporting the relevant microplate are made apart from each other.

Figure 8:
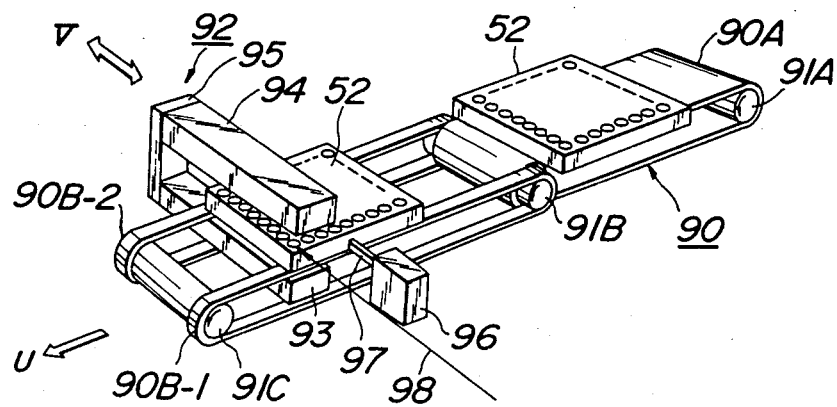
FIG. 8 is a perspective view showing a reaction line path and photometering part according to the invention.

As shown in FIG. 8, the endless belt 90 is moved in an arrow U direction by means of driving shafts 91A, 91B and 91C which are rotated at a constant speed quietly by a given driving means. The endless belt 90 is moved intermittently at a pitch distance between the reaction vessels 8-1 to 8-10, since in a photometering portion 92 the photometry is performed per one sample solution in the reaction vessels 8-n-1 to 8-n-12 on the microplate 52. In this embodiment, this traveling line is called a third reaction line path. The belt 90 comprises a belt 90A having a sufficient width for traveling the microplate 52 and a pair of belts 90B-1 and 90B-2 which are made apart so as not to affect a twelve-channel photometry for the reaction vessels via a space formed therebetween. These belts 90A and 90B-1, 90B-2 are wound around driving shaft 91B apart by a given distance therebetween so as not to affect the traveling of these belts each other.

In FIGS. 6 and 8, the photometering portion 92 comprises a light source portion 93, a light receiving means 94 and a supporting means 95, and the light source portion 93 and the light receiving means 94 are secured to the supporting means 95 on both sides of the third reaction line path. On the third reaction line path, the positioning for one series of twelve reaction vessels is performed by using a positioning member 97 of a positioning control device 96 arranged at a predetermined position near the photometering portion 92. The positioning member 97 cooperates with notches formed in the side wall of the microplate 52 with a pitch corresponding to the pitch of the reaction vessel arrays.

In this embodiment, a microplate traveling time period from the reagent delivering position 58 to this photometering position 98 i.e. the reaction time period is 60 minutes. The supporting means 95 is moved reciprocatively in an arrow V direction perpendicular to an arrow U direction, and thus the photometry for all the twelve reaction vessels (channels) is effected successively at the photometering position 98. The photometry for the reaction vessels on the microplate 52 may be performed either in one direction or both directions.

Figure 9:
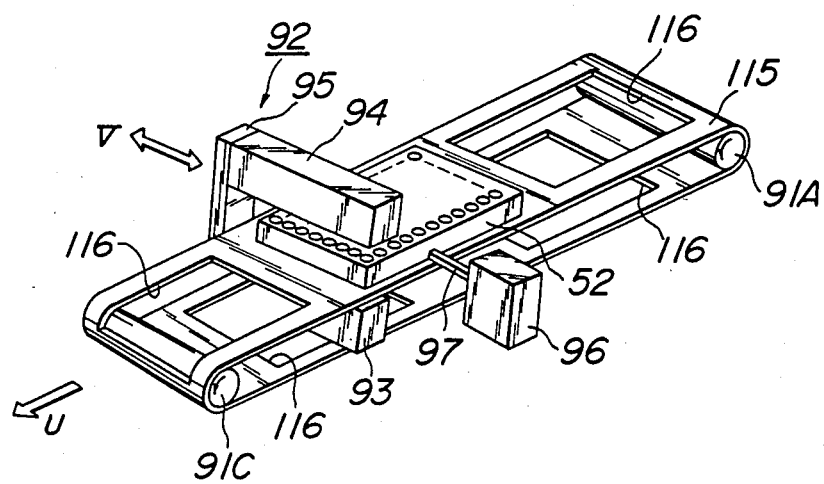
FIG. 9 is a perspective view illustrating another embodiment of the reaction line path shown in FIG. 8.

Moreover, as shown in FIG. 9, it is possible to construct the third reaction line path in such a manner that an endless belt 115 is moved in the arrow U direction by a pair of driving shafts 91A, 91C, and a plurality of openings 116 are formed in this endless belt 115 so as to travel effectively the microplate 52 on the endless belt 115 and to receive the light flux emitted from the light source portion 93 by the light receiving means 94 effectively through the opening. In addition, it is possible to cover the opening with a transparent member having good light transmittivity so as to improve the supporting ability of the microplate 52.

In FIGS. 6 and 2, the microplate 52 after photometry is fed to an ascending device 120 and is mounted on a plate 121, and then the microplate 52 on the plate 121 is moved by a driving means 122 upward in an arrow W direction along an ascending line 123. Next, when the microplate 52 reaches a predetermined stop position 124, the driving means 122 is stopped. At this position the microplate 52 may be observed by a viewer device 126 with the naked eye, if necessary. The thus observed microplate 52 is further fed to a piling device 127 by for example the traveling of the plate 121 of the ascending device 120 or a feeding mechanism, and is piled up successively in an arrow Y direction by means of a plate 129 driven by a driving means 128.

Figure 10:
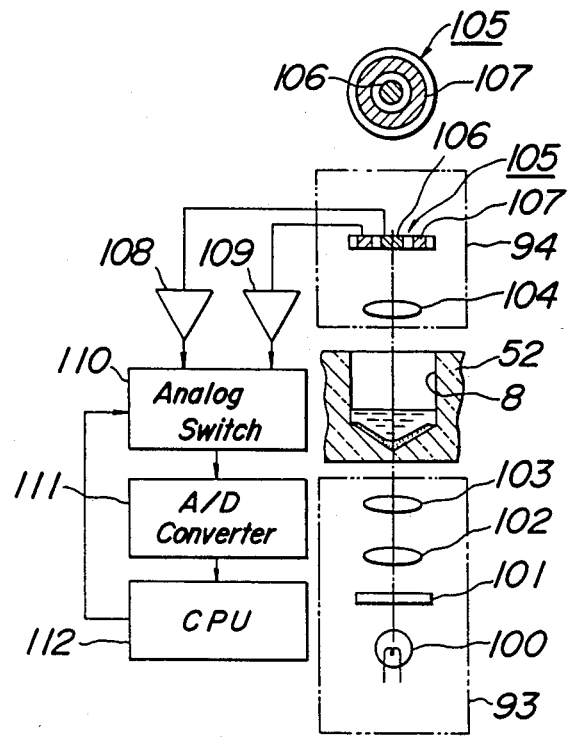
FIG. 10 is a schematic view illustrating a detail construction of the photometering part shown in FIGS. 6 and 8.

Then, a construction of the photometering portion 92 and a detecting operation will be explained. FIG. 10 is a schematic view showing one embodiment of the light source portion 93 and the light receiving means 94 shown in FIGS. 6 and 8. In the light source portion 93, a light flux emitted from a light source lamp 100 is projected uniformly onto the bottom surface of the reaction vessel 8 in the microplate 52 through a heat absorbing filter 101, a condenser lens 102 and an illumination lens 103. In the light receiving means 94, a uniformly illuminated image of the bottom surface of the reaction vessel 8 is received by a light receiving device 105 through an objective lens 104. The light receiving device 105 comprises two concentrical light receiving elements 106 and 107 which are arranged concentrically apart with each other as shown by a plan view in FIG. 10. In this embodiment, photoelectrically converted outputs of these light receiving elements 106 and 107 are amplified by amplifiers 108 and 109, respectively, and thus amplified outputs are supplied to a CPU 112 through an analog switch 110 and an A/D converter 111.

In this embodiment, since the bottom surface of respective reaction vessels 8 has a conical shape, in case of agglutination reaction the uniformly deposited pattern is formed on the bottom surface, and in case of non-agglutination reaction the integrated pattern is formed at the bottom center. Therefore, if the particle pattern formed on the bottom surface of the reaction vessel 8 is scanned by moving the photometering portion 92 with respect to the reaction vessel, in case of the uniformly deposited pattern, a photoelectrically converted output from the element 106 becomes large near a center portion of the reaction vessel 8 as shown in FIG. 11A due to a thickness variation of the bottom, and in case of the integrated pattern, a photoelectrically converted output from the element 106 becomes small near the center portion of the reaction vessel 8 as shown in FIG. 11B.

In FIGS. 11A and 11B, the photoelectrically converted output may be sampled from a starting point 1 to an ending point N' over the whole diameter of the reaction vessel 8, and the thus sampled outputs may be supplied to the CPU 112. However, in this embodiment, a sampling region from $n_1$ to $n_2$ whose center is almost the same as that of the reaction vessel 8 and whose diameter is smaller than that of the reaction vessel is determined, and photoelectrically converted output of the light receiving element 106 is sampled at n positions having the same interval (1 $\mu$m to 100 $\mu$m). At the same time the output of the light receiving element 107 is also sampled. Then the sampled outputs are supplied to the CPU 112. The sampling region may be determined with taking into account of an improvement of analysis accuracy and a shortening of scanning period. Moreover, the number of samplings n of the photoelectrically converted output is previously determined by taking into account of various requirements such as analysis accuracy, diameter of the reaction vessel 8, shape of agglutination pattern, scanning distance, reagent, etc., and for example, the number of samplings n may be several tens to one hundred if the diameter of the reaction vessel 8 is assumed about 5 mm to 10 mm.

Figure 12:
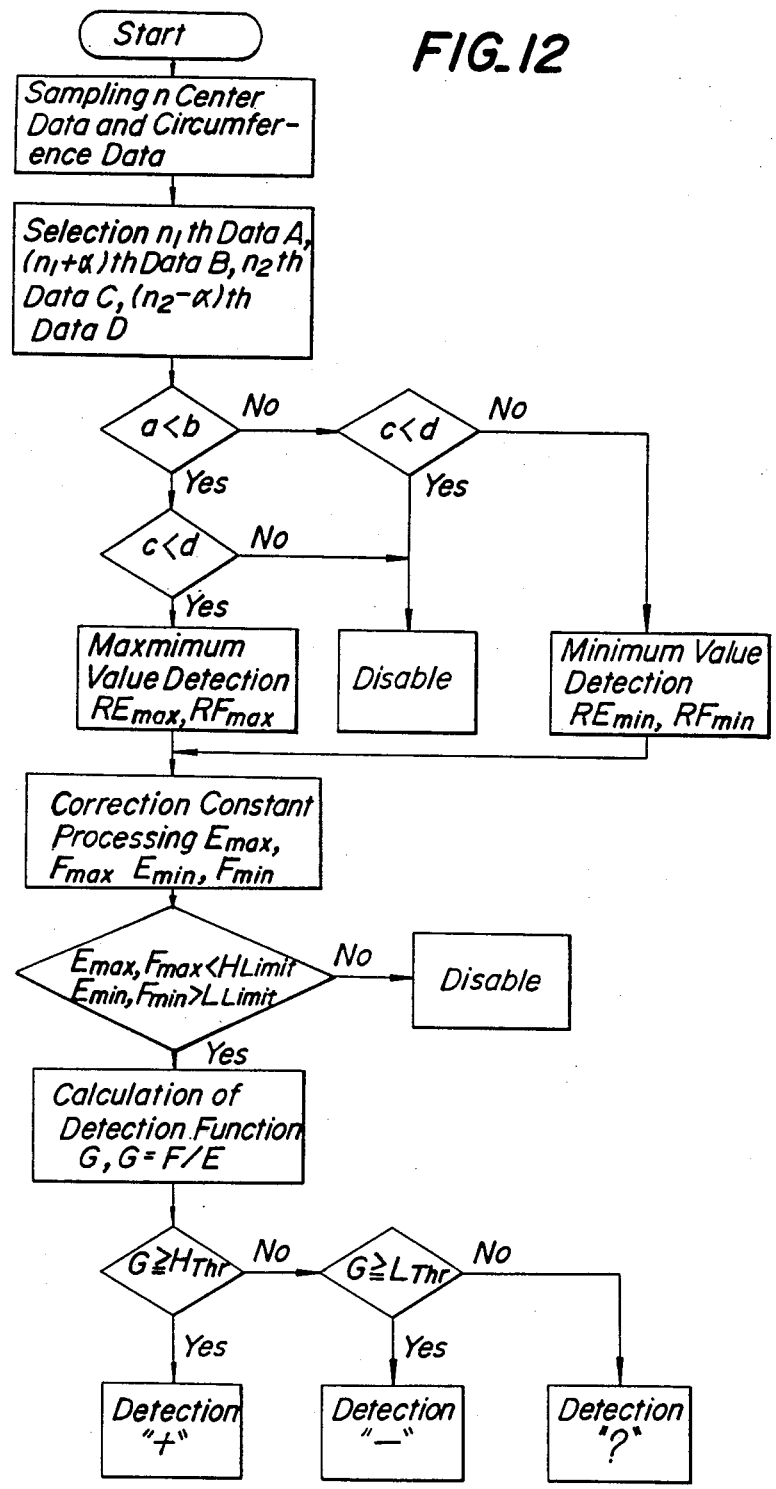
FIG. 12 is a flow chart showing successive procedures for detecting an agglutination pattern on the basis of an output of the light receiving device.

Hereinafter, the detecting operation according to the invention will be explained with reference to a flowchart shown in FIG. 12. In this embodiment, the photoelectrically converted output of the light receiving element 106 is called a center data, and that of the light receiving element 107 is called a circumference data.

At first, after generating the center and circumference data, it is detected whether the pattern of the center data is "upward convex" (FIG. 11A) or "downward convex" (FIG. 11B). This detection is performed as follows. At first, $n_1$th center data a is compared with $(n_1+\alpha)$th center data b ($\alpha < n/2$), and also $n_2$th center data c is compared with $(n_2-\alpha')$th center data d ($\alpha' = \alpha$ or $\alpha' < n/2$). Then, if the condition is a<b and c<d, the pattern is detected as "upward convex", if a>b and c>d, "downward convex" and if a<b and c>d, or a<b and c<d, the judgement is made disable (final result is "?").

If the detection is "upward convex", then a maximum value of the center data is detected. Contrary to this, if the detection is "downward convex", then a minimum value of the center data is detected. In the maximum value detection, at first the maximum value ($RE_{max}$) in the n center data values is detected and then from the circumference data (RF) derived from the light receiving element 107 at a position corresponding to that of the maximum center data value $RE_{max}$. In this case, if the maximum value is detected at more than two points, the data value which is obtained at a point nearer to $(n/2-1)$th or $(n/2-2)$th, $(n/2+1)$th or $(n/2+2)$th point is assumed to be the maximum value (if distances of these points are identical, younger ordering value is assumed to be the maximum value). In this embodiment, $RE_{max}$ and RF, and two values adjacent to $RE_{max}$ and RF are respectively averaged to derive the center $RE_{max}$ and the circumference $RF_{max}$. Moreover in the minimum value detection, as is the same as the maximum value detection, at first the minimum center value ($RE_{min}$) and the corresponding circumference data value (RF) are detected and then two values adjacent to the detected value ($RE_{min}$) and two values adjacent to the detected value (RF) are derived. Finally, $RE_{min}$ and RF, and two values adjacent to $RE_{min}$ and RF are respectively averaged to derive the center value $RE_{min}$ and the circumference value $RF_{min}$.

The photometered data thus detected have different spans due to a difference of the light receiving area of the light receiving elements 106 and 107, and thus the photometered data are multiplied with correction constants to make both spans to be identical, so that $E_{max}$, $F_{max}$ or $E_{min}$, $F_{min}$ are obtained.

Then, it is detected whether the corrected photometered data $E_{max}$, $F_{max}$ or $E_{min}$, $F_{min}$ are within a predetermined range from L.Limit to H.Limit (shown in FIGS. 11A and 11B) or not. In this case, if the condition is L.Limit$<E_{max}$, $F_{max}$ or $E_{min}$, $F_{min}<$H.Limit, then a detection function G is calculated, and if $E_{max}$, $F_{max} \geq$ H.Limit or $E_{min}, F_{min} \leq$ L.Limit, then the final detection is "?".

As for the detection function G, use is made of a ratio $G=F/E$, where E is a corrected center data and F is a corrected circumference data. Moreover, it is possible to use as the detection function G, F-E, log (F/E), log (F-E), log (F-QE) where Q is a constant, etc.

Then, the calculated value is compared with predetermined high threshold H.Thr and low threshold L.Thr. In this case, if the condition is G$\geq$H.Thr, that is, "non-agglutination", the detection is "+", if G$\leq$L.Thr, that is, "agglutination", then the detection is "−" and if L.Thr$<$G$<$H.Thr, the detection is "?". If the threshold level H.Thr is made high in excess, the accuracy for the detection "+" becomes high, but a percentage of an occurrence of the detection "?" becomes large correspondingly. Moreover, if the threshold level L.Thr is made low in excess, the accuracy for the detection "−" becomes high, but in the same manner the percentage of the detection "?" becomes large correspondingly. Therefore, these threshold levels H.Thr and L.Thr must be suitably determined with taking into account of various conditions such as the detection function G, the reagent, the sample, an environmental condition, the detection accuracy, etc.

In this embodiment, the detection result is printed out by a printer under the control of the CPU 112 together with various information previously read out by the sample detecting device 30 such as the sample information and the sample existent information detected by a pair of electrodes consisting of the electrode 35 and the electrode nozzle 33 or 34.

FIG. 13 is a flow-chart showing successive operations of the analyzing apparatus mentioned above, and since the detailed explanation thereof is clearly understood from the above, the explanation is omitted here.

Moreover, in the above explanation, a microplate traveling period from the reagent delivering position 58 to the photometering position 98 i.e. the reaction time period is assumed 60 minutes, but it is possible to make the reaction time period 30 minutes by making the rotation speed of the supporting belts 81A, 81B in the microplate descending device 80 faster and by inserting the microplates 52 into every two plates 81A-n to 81B-n.

According to the invention, various advantages can be obtained as follows.

(1) Since a manual operation is required a little and thus any skill is required for the operator, it is possible to make the apparatus automatic and the analyzing accuracy high.

(2) It is possible to make an amount of the sample solution and the reagent to be used small.

(3) It is possible to effect the detections for a plurality of samples and test-items in a short time period.

(4) Since the reaction line is arranged three-dimensionally, it is possible to make the whole apparatus small in size.

(5) Since use is made of the sample detecting device 30, it is possible to prevent a handling miss of the sample, and to compare the results automatically detected by the analyzer with ABO-type previously read out of the bar code.

(6) Since the direct and the indirect judgements are performed at the same time, it is possible to improve a reliability of the blood-type judgement.

(7) Since the analyzing results are indicated together with the sample existent information, it is possible to distinguish easily the difference between the disable judgement for a normal sample and that due to the no sample.

What is claimed is:

1. An apparatus for analyzing an immunological agglutination reaction in blood samples comprising:
   (a) a plurality of sample tubes for containing blood samples including separated blood cells and serum to be analyzed;
   (b) means for carrying said plurality of sample tubes in a first direction to a sample delivery position;
   (c) a sample plate containing at least three diluting vessels;
   (d) means, independent of said sample tube carrying means, for carrying said sample plate of diluting vessels in said first direction through said sample delivery position and a diluted sample delivery position;
   (e) means for forming at least one diluted blood cell sample, and at least two diluted serum samples having different dilution rates, by separately delivering blood cells and serum contained in one of said plurality of sample tubes situated at said sample delivery position into said at least three diluting vessels situated at said sample delivery position together with a diluent;
   (f) a reaction line extending in said first direction including an entrance and a plurality of continuous reaction line passages extending vertically and horizontally in a vertical plane;
   (g) a plurality of microplates;
   (h) means for successively feeding at least one microplate in said first direction into said entrance of said reaction line, said microplate having a multiplicity of reaction vessels arranged in a plurality of rows aligned in a second direction perpendicular to said first direction, each said row containing a plurality of reaction vessels necessary for determining blood type;
   (i) means for quantitatively simultaneously sucking the diluted blood cell sample and the at least two diluted serum samples contained in said diluting vessels situated at said diluted sample delivery position and successively discharging each of the samples into two of said plurality of reaction vessels of one of said rows of said at least one microplate supplied on said reaction line, said sucking and discharging means including a linearly and vertically moveable supporting arm and a rotatable delivery arm pivotally connected to said supporting arm, said delivery arm having secured thereto a plurality of nozzles equal in number to the number of diluting vessels in said sample plate;

(j) means for quantitatively simultaneously delivering reagent into said plurality of reaction vessels of said one row according to an analysis-item to be tested;

(k) means for transporting said at least one microplate having blood samples and reagent delivered in said multiplicity of reaction vessels along said reaction line in a substantially stable manner;

(l) means for photoelectrically detecting an agglutination pattern formed on an inclined bottom surface of said multiplicity of reaction vessels at a measuring position on the reaction line due to an antigen and antibody reaction of the blood cell sample and the serum samples with said reagent;

(m) means for moving said photoelectric detection means in the direction of each said row of reaction vessels so as to obtain a plurality of photoelectrically converted signals of a sample substantially simultaneously;

(n) means for receiving said photoelectrically converted signals to effect an analysis due to said agglutination pattern; and (o) means for discharging said at least one microplate from an exit of said reaction line after an agglutination pattern formed in each of said multiplicity of reaction vessels in said at least one microplate has been detected.

2. The apparatus of claim 1, wherein said sample tube carrying means comprises:
a device for intermittently transporting a cassette tray having a plurality of detachably mounted racks, each of said racks including a plurality of sample tubes; and
a device for carrying one of said plurality of racks from said cassette tray to said sample delivery position and for carrying said rack back to said cassette tray.

3. The apparatus of claim 2, wherein said rack carrying device reciprocates said rack along a rack traveling path which is parallel to a path along which said diluting vessels are fed.

4. The apparatus of claim 1, wherein said sucking and discharging means further comprises:
a device for sucking diluted blood cell and serum samples into said nozzles; and
a device for selectively discharging the diluted blood cell and serum samples from said nozzles into a given reaction vessel in said array while said nozzles are in motion along said array.

5. The apparatus of claim 4, wherein said reagent delivering means comprises:
a device that coacts with said sample delivering means for discharging reagent into said reaction vessels in said array substantially simultaneously with samples.

6. The apparatus of claim 1, wherein said microplate transporting means comprises:

a first feeding device for feeding a microplate in a horizontal plane through said diluted sample delivery position and said reagent delivery position;
a second feeding device for descending said microplate in a vertical direction;
a third feeding device for transporting said microplate in a horizontal direction through said measuring position; and
a fourth feeding device for ascending said microplate in a vertical direction.

7. The apparatus of claim 6, wherein said second microplate feeding device comprises endless belts having L-shaped plates for holding and accommodating a plurality of said microplates by stacking them in a vertical direction by engaging a rear surface of said microplates with said L-shaped plates.

8. The apparatus of claim 1, further comprising an observation device for visibly observing a microplate at an uppermost position of said fourth feeding device.

9. The apparatus of claim 1, further comprising a plurality of sample plates, each said sample plate containing at least three diluting vessels, and wherein said diluting vessel carrying means comprises an endless belt rotating through said sample delivery position, said diluted sample delivery position and a washing position, said apparatus further comprising a member for coupling said sample plates to said endless belt.

10. The apparatus of claim 9, wherein said diluting vessels are detachably mounted on said sample plates.

11. The apparatus of claim 9, wherein four diluting vessels are mounted on each of said sample plates.

12. The apparatus of claim 11, wherein said diluted sample forming means comprises:
a first delivery device for sucking blood cells contained in one of said plurality of sample tubes situated at said sample delivery position and quantitatively discharging an amount of the sucked blood cells into a first diluting vessel on one of said sample plates at said sample delivery position;
a second delivery device for sucking serum contained in said sample tube and quantitatively discharging an amount of the sucked serum into a second, a third and a fourth diluting vessel on said one of said sample plates;
a first diluent discharge device for quantitatively supplying an amount of diluent into said first diluting vessel; and
a second, a third and a fourth diluent discharge device for quantitatively supplying an amount of diluent into said second, third and fourth diluting vessels, respectively.

13. The apparatus of claim 12, wherein said first delivery device and said first diluent discharge device are operated substantially simultaneously.

14. The apparatus of claim 13, wherein said second, third and fourth diluent discharge devices can be operated before said sucked serum is delivered into said second, third and fourth diluting vessels.

15. A method for analyzing an immunological agglutination reaction in blood samples comprising:
carrying a plurality of sample tubes containing blood samples including separate blood cells and serum to be analyzed in a first direction to a sample delivery position;
carrying, independently of said sample tubes, a sample plate containing a plurality of diluting vessels in said first direction through said delivery position and a diluted sample dilivery position extending in said first direction, said sample plate containing at least three diluting vessels;

separately delivering, together with a diluent, said blood cells and said serum contained in one of said plurality of sample tubes situated at said sample delivery position into said at least three diluting vessels situated at said sample delivery position, so as to form at least one diluted blood cell sample and at least two diluted serum samples having different dilution rates;

carrying said diluted blood cell sample and said diluted serum samples in the first direction to said diluted sample delivery position;

feeding at least one microplate into an entrance of a reaction line, extending in said first direction, to a reagent delivery position perpendicular to said first direction, said at least one microplate having a multiplicity of reaction vessels arranged in a plurality of rows aligned in a second direction perpendicular to said first direction, each said row containing a plurality of reaction vessels necessary for determining blood type;

linearly moving and rotating a row of delivery nozzles, equal in number to the number of diluting vessels in said sample plate, from a rest position perpendicular to said first direction to said diluted sample delivery position above said at least three diluting vessels situated at said diluted sample delivery position, said row of delivery nozzles being secured to a rotatable delivery arm which is pivotally connected to a linearly and vertically moveable supporting arm;

moving said delivery nozzles downward until they are in proper position with respect to said diluting vessels, and quantitatively, simultaneously sucking said diluted blood cell sample and said diluted serum samples from said diluting vessels;

moving said delivery nozzles upward away from said diluting vessels;

linearly moving and rotating said delivery nozzles from said diluted sample delivery position to said reagent delivery position above one of said rows of reaction vessels situated at the reagent delivery position;

moving said delivery nozzles downward until they are in proper position with respect to said one row of reaction vessels, and successively delivering each of said samples into two of said plurality of reaction vessels of said one row;

quantitatively, simultaneously delivering reagent into said plurality of reaction vessels of said one row according to an analysis-item to be tested;

moving said delivery nozzles upward away from said one row of reaction vessels;

vertically and horizontally conveying said at least one microplate having blood samples and reagent along the reaction line while simultaneously reacting the blood samples and reagent;

photoelectrically detecting an agglutination pattern formed on an inclined bottom surface of said multiplicity of reaction vessels at a measuring position on said reaction line due to an antigen and antibody reaction of said blood cell sample and said serum samples with said reagent, by moving a photoelectric measuring means in the direction of each said row so as to obtain a plurality of photoelectrically converted signals of a sample substantially simultaneously;

receiving said photoelectrically converted signals to effect an analysis due to said agglutination pattern; and discharging said at least one microplate from an exit of said reaction line after an agglutination pattern formed in each of said multiplicity of reaction vessels in said microplate has been detected.

16. The method of claim 15 wherein said blood cell sample and said serum samples are selectively discharged into said one row of reaction vessels of said microplate perpendicular to said first direction while said delivery nozzles are moved along said one row.

17. The method of claim 15 wherein:
said plurality of sample tubes are intermittently transported in a detachably mounted rack of a cassette tray, said cassette tray having a plurality of such detachably mounted racks; and
said plurality of sample tubes are carried in said rack from said cassette tray to said sample delivery position and back to said cassette tray.

18. The method of claim 15 wherein said sample plate is coupled to an endless belt which rotates through said sample delivery position and said diluted sample delivery position.

19. The method of claim 18 wherein:
an amount of said blood cells is sucked from said one of said plurality of sample tubes situated at said sample delivery position and quantitatively discharged, together with diluent, into a first diluting vessel on said sample plate at said sample delivery position; and
an amount of said serum is sucked from said one of said plurality of sample tubes and quantitatively discharged, together with diluent, into a second, a third and a fourth diluting vessel on said sample plate.

* * * * *